(12) United States Patent
Huang et al.

(10) Patent No.: US 10,213,175 B2
(45) Date of Patent: Feb. 26, 2019

(54) HEAT SINKING SYSTEM AND IMAGING APPARATUS INCLUDING THE SAME

(71) Applicant: General Electric Company, Schenectady, NY (US)

(72) Inventors: Duzi Huang, Beijing (CN); Weimin Qu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 193 days.

(21) Appl. No.: 15/127,309

(22) PCT Filed: Feb. 27, 2015

(86) PCT No.: PCT/US2015/018101
§ 371 (c)(1),
(2) Date: Sep. 19, 2016

(87) PCT Pub. No.: WO2015/142499
PCT Pub. Date: Sep. 24, 2015

(65) Prior Publication Data
US 2018/0103919 A1  Apr. 19, 2018

(30) Foreign Application Priority Data
Mar. 19, 2014 (CN) .......................... 2014 1 0104440

(51) Int. Cl.
*A61B 6/03* (2006.01)
*A61B 6/00* (2006.01)

(52) U.S. Cl.
CPC ............ *A61B 6/4488* (2013.01); *A61B 6/032* (2013.01); *A61B 6/035* (2013.01)

(58) Field of Classification Search
CPC .. A61B 6/00; A61B 6/03; A61B 6/032; A61B 6/4488; A61B 6/035
(Continued)

(56) References Cited

U.S. PATENT DOCUMENTS 5,761,269 A    6/1998  Sugihara et al.
2004/0228450 A1  11/2004  Mueller
(Continued)

FOREIGN PATENT DOCUMENTS

DE    102008021168 A1    11/2009
JP       2003260048 A     9/2003

OTHER PUBLICATIONS

International Search Report and Written Opinion for corresponding PCT application PCT/US2015/018101 dated May 15, 2015; 12 pages.

*Primary Examiner* — Jurie Yun

(57) ABSTRACT

A heat sinking system and an imaging apparatus including the heat sinking system. The heat sinking system includes an air introducing portion, a capture portion and an air discharge portion. The air introducing portion is configured to introduce air from external, and to be in communication with heat sinking space, so that the introduced air flows into the heat sinking space and exchanges heat with a heat sinking object which is accommodated in the heat sinking space. The capture portion is configured to be in communication with the heat sinking space and the air discharge portion, and to capture air which flows from the heat sinking space to the capture portion and enable the captured air to flow into the air discharge portion. The air discharge portion is configured to discharge the air which flows in out of the capture portion to the external.

12 Claims, 9 Drawing Sheets

(58) Field of Classification Search
USPC .......................................... 378/4, 210, 199
See application file for complete search history.

(56) References Cited

U.S. PATENT DOCUMENTS

| 2009/0232281 | A1* | 9/2009 | Jimbo | A61B 6/035 |
| | | | | 378/199 |
| 2015/0320376 | A1* | 11/2015 | Oishi | A61B 6/4405 |
| | | | | 378/199 |

* cited by examiner

HEAT SINKING SYSTEM AND IMAGING APPARATUS INCLUDING THE SAME

This application is a filing under 35 U.S.C. 371 of international application number PCT/US2015/018101, filed Feb. 27, 2015, which claims priority to China application number 201410104440.1, filed Mar. 19, 2014, the entire disclosure of each of which is hereby incorporated by reference.

TECHNICAL FIELD

The present invention relates to the imaging field, and more particularly to a heat sinking system and an imaging apparatus including the same.

BACKGROUND ART

A Computed Tomography (CT) apparatus generally includes an X-ray imaging device, and a gantry to accommodate and support the X-ray imaging device. The X-ray imaging device comprises an X-ray generator to generate X-rays and emit the generated X-rays to an aim object (for example, a patient to be diagnosed) and an X-ray detector to receive X-rays passing through the aim object and convert the received X-rays into electrical signals. In addition, the CT apparatus may further comprise a processor for receiving the electrical signals generated by the X-ray generator and processing the received electrical signals to generate an image, and a display for displaying the generated image.

Elements, for example, an X-ray generator, included in the X-ray imaging device, need to be operated under appropriate temperature conditions, so as to ultimately acquire an image of a desired quality. Therefore, in order to guarantee quality of the image acquired, the CT apparatus further includes a heat sinking system disposed within the gantry to perform heat sinking on the X-ray imaging device.

SUMMARY OF THE INVENTION

The object of exemplary embodiments of the present invention is to overcome the above-mentioned and/or other problems underlying the prior art. Therefore, the exemplary embodiments of the present invention provide a heat sinking system capable of increasing heat sinking efficiency and an imaging apparatus including the heat sinking system.

According to an exemplary embodiment, a heat sinking system is provided. The heat sinking system includes an air introducing portion, a capture portion and an air discharge section. The air introducing portion is configured to introduce air from external, and to be in communication with heat sinking space, so that the introduced air flows into the heat sinking space and exchanges heat with a heat sinking object which is accommodated in the heat sinking space. The capture portion is configured to be in communication with the heat sinking space and the air discharge portion, and to capture air which flows from the heat sinking space to the capture portion and enable the captured air to flow into the air discharge portion. The air discharge portion is configured to discharge the air which flows in out of the capture portion to the external.

According to an exemplary embodiment, an imaging apparatus is provided. The imaging apparatus includes a gantry and an imaging device. The gantry includes a heat sinking system as described above. The imaging device is disposed and accommodated in heat sinking space of the heat sinking system as a heat sinking object, to exchange heat with air which flows in out of an air introducing portion.

Through the following detailed description, drawings and claims, other features and aspects will become apparent.

DETAILED DESCRIPTION OF THE EMBODIMENTS

Hereinafter, specific embodiments of the present invention will be described. It is to be noted that, during the process of detailed description of these embodiments, for the sake of concise and clear description, the present description can not possibly describe in detail all features of practical embodiments. It should be understood that, during the process of actual implementation of any embodiment, just as in the process of any engineering or design project, in order to achieve developers' specific purposes and meet system-related or business-related constraints, it is customary to make a variety of specific decisions, which also involves a change from one embodiment to another embodiment or the other way around. In addition, it should also be understood that, although efforts made in such developing process might be complex and lengthy, persons of ordinary skill in the art associated with the disclosure of the present invention find it nothing but conventional techniques to make modifications in some design, manufacturing, production or the like on the basis of the technical contents disclosed by the present disclosure; and the present disclosure shall not be construed to be insufficient.

Unless defined otherwise, technical terms or scientific terms used in the claims and the description shall carry conventional meanings as construed by persons of ordinary skill in the art which the present invention pertains to. The "first", "second", and the like used in the description and the claims of the patent application for an invention do not denote any order, quantity, or importance, but are simply used to make a distinction between different components. The expressions "one", "a"/"an" or the like do not intend to limit the quantity, but indicate presence of at least one. Such expressions as "comprise", "include" and the like mean that an element or object present prior to the "comprise" or "include" covers elements or objects listed subsequent to the "comprise" or "include" and their equivalent elements, not excluding other elements or objects. The expression "connect" or the like is neither limited to physical or mechanical connection, nor limited to direct or indirect connection.

Figure 1:
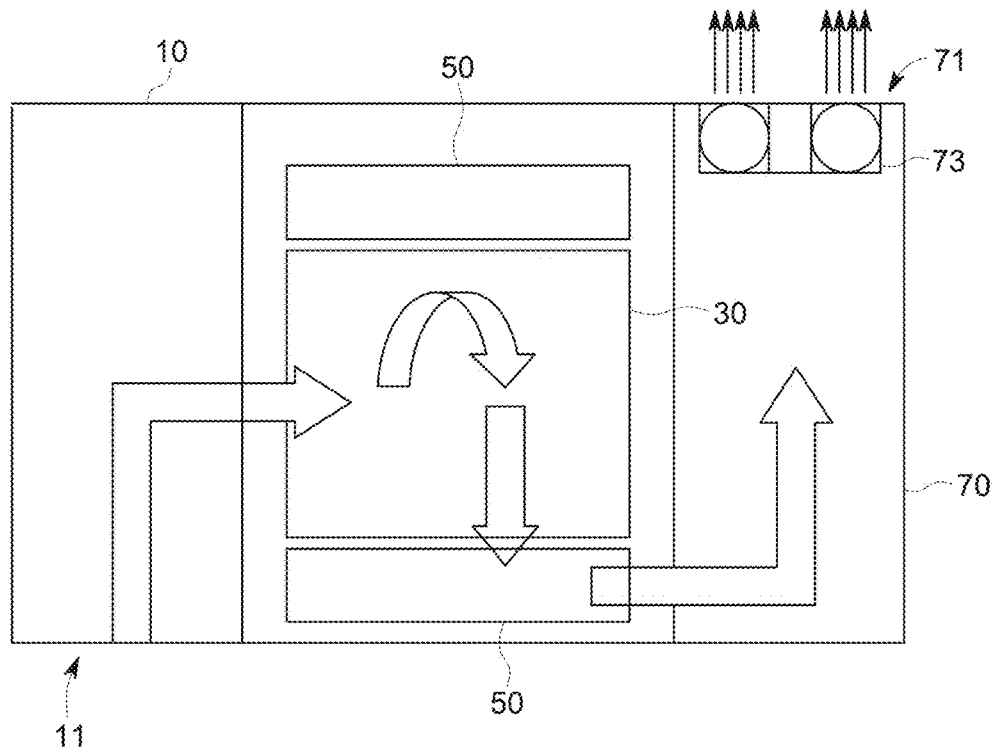
FIG. 1 is a schematic view illustrating a heat sinking system according to an exemplary embodiment.

FIG. 1 is a schematic view illustrating a heat sinking system according to an exemplary embodiment. As shown in FIG. 1, the heat sinking system according to the exemplary embodiment may include an air introduction portion 10, heat sinking space 30, a capture portion 50 and an air discharge portion 70. Further, a path of air flow is shown with arrows in FIG. 1.

The air introduction portion 10 can introduce air from external of the heat sinking system. For example, the air introducing portion 10 may include an air inlet 11 disposed at the bottom of the heat sinking system. However, the exemplary embodiment is not limited thereto, for example, the air inlet 11 may be provided at different positions as needed, and a plurality of air inlets 11 may be provided. The air introducing portion 10 may be in communication with the heat sinking space 30. Thus, air introduced via the air inlet 11, for example, can flow into the heat sinking space 30.

The heat sinking space 30 can accommodate a heat sinking object. Herein, the heat sinking object may include an imaging device, for example, an X-ray imaging device. However, the exemplary embodiment is not limited thereto, for example, the heat sinking object may further include a drive means to rotate the imaging device in the heat sinking space 30, and the like. Air introduced via the air introducing portion 10 can flow into the heat sinking space 30, and exchanges heat with the heat sinking object. Then, the air which has exchanged heat with the heat sinking object can flow into the capture portion 50 and is captured by the capture portion 50.

The capture portion 50 can be in communication with the heat sinking space 30 and the air discharge portion 70. The capture portion 50 can allow air to flow in a first direction from the heat sinking space 30 to the air discharge portion 70 and can prevent the air from flowing in a second direction from the air discharge portion 70 to the heat sinking space 30 and opposite to the first direction. That is, the capture portion 50 can "capture" air flowing from the heat sinking space 30 to the capture portion 50, and can enable the captured air to flow into the air discharge portion. To this end, the capture portion 50 can include capture guide members. The capture guide members can be configured according to the aerodynamics principle, so that they have a structure making it possible to allow the air to flow in a single direction.

The air discharge portion 70 may be in communication with the capture portion 50, thereby discharging air which flows in out of the capture portion 50 to the external. For example, the air discharge portion 70 may include an air outlet 71 disposed at the top of the heat sinking system. However, the exemplary embodiment is not limited thereto, for example, the air outlet 71 may be provided at different positions as needed, and a plurality of air outlets 71 may be provided. In addition, as shown in FIG. 1, the air discharge portion 70 may include a fan 73 for blowing air in the air discharge portion 70 to the external. For example, the fan 73 may be disposed at the air outlet 71. Although not shown in FIG. 1, a fan can also be disposed at the air introducing portion 10, so as to blow air from the external to the air introducing portion.

According to the exemplary embodiment, the heat sinking system may allow air in the heat sinking space to flow into the air discharge portion in a single direction. Therefore, as compared with a conventional heat sinking system, the heat sinking system according to the exemplary embodiment significantly improves heat sinking efficiency. This will be described below in more detail.

Figure 2:
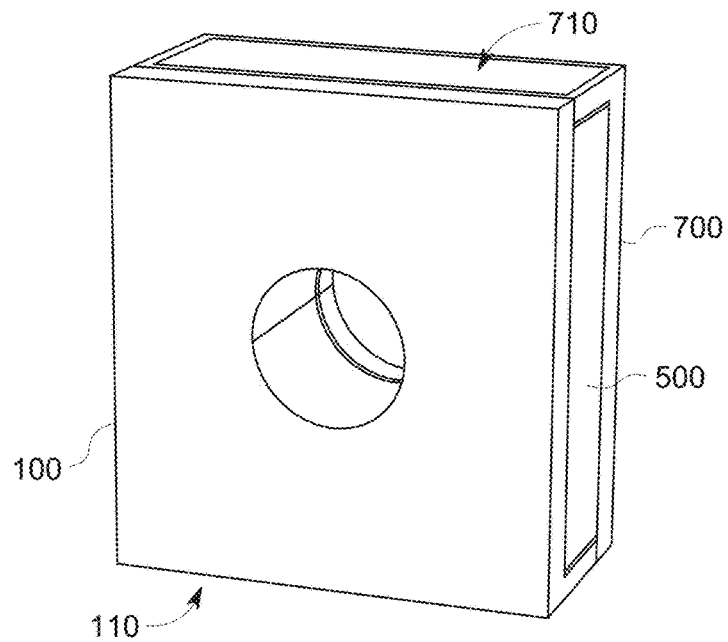
FIG. 2 is a perspective view illustrating a heat sinking system according to an exemplary embodiment.
Figure 3:
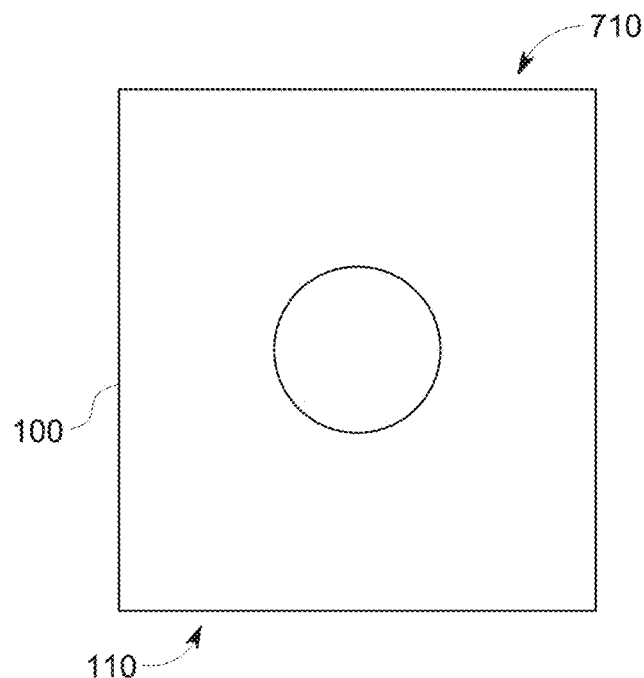
FIGS. 3 to 5 are respectively a front view, a top view and a bottom view illustrating a heat sinking system according to exemplary embodiments.
Figure 4:
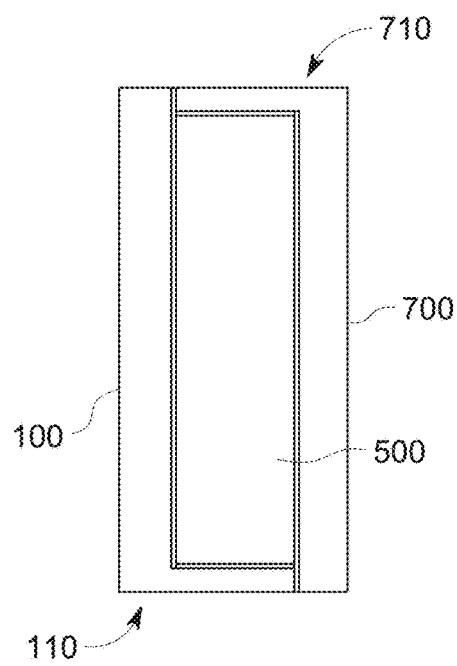
Figure 5:
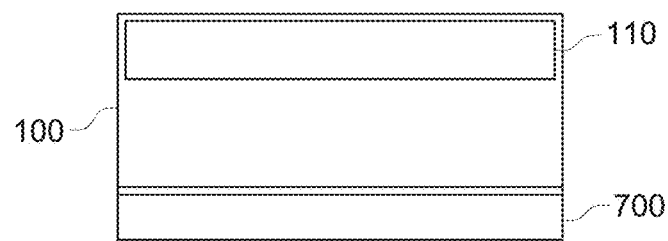
Figure 6:
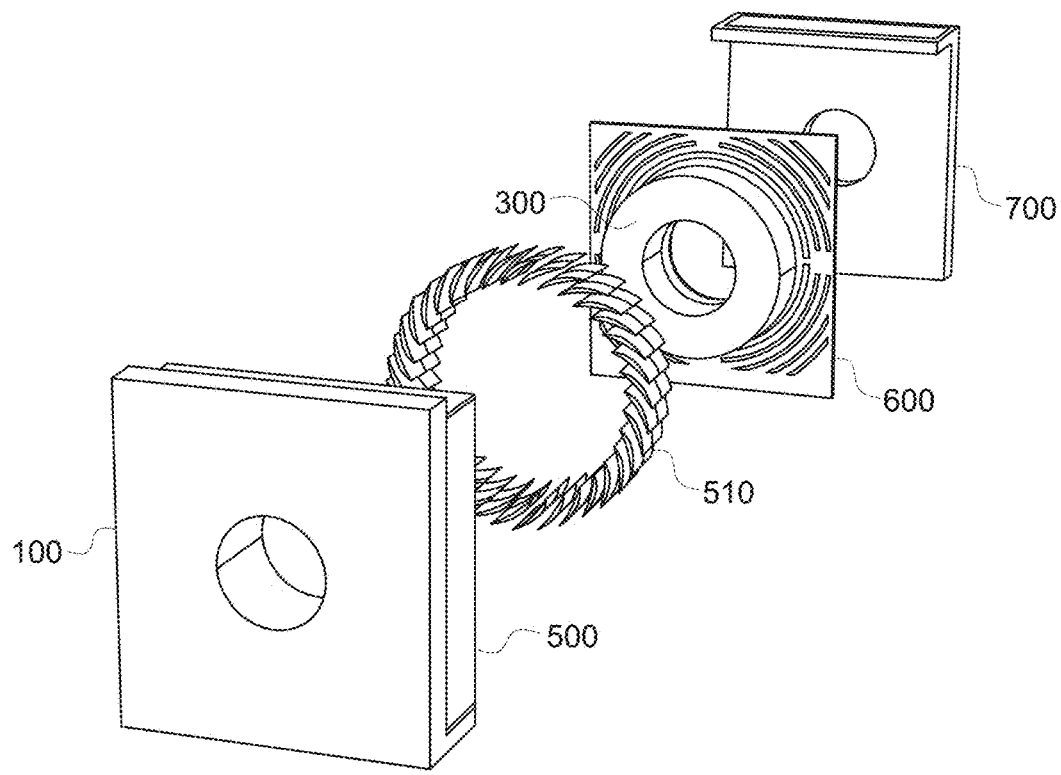
FIG. 6 is an exploded perspective view illustrating a heat sinking system according to an exemplary embodiment.

Hereinafter, optional/preferred embodiments of a heat sinking system according to exemplary embodiments will be described in detail with reference to FIGS. 2 to 14. FIG. 2 is a perspective view illustrating a heat sinking system according to an exemplary embodiment. FIGS. 3 to 5 are respectively a front view, a top view and a bottom view illustrating a heat sinking system according to exemplary embodiments. FIG. 6 is an exploded perspective view illustrating a heat sinking system according to an exemplary embodiment.

As shown in FIGS. 2 to 6, the heat sinking system according to the exemplary embodiments may include an air introduction portion 100, heat sinking space 300, a capture portion 500 and an air discharge portion 700.

The air introduction portion 100 can introduce air from external of the heat sinking system. For example, the air introducing portion 100 may include an air inlet 110 disposed at the bottom of the heat sinking system. However, the exemplary embodiments are not limited thereto, for example, the air inlet 110 may be provided at different positions as needed, and a plurality of air inlets 110 may be provided. The air introducing portion 100 may be in communication with the heat sinking space 300. Thus, air introduced via the air inlet 110, for example, can flow into the heat sinking space 300.

The heat sinking space 300 can accommodate a heat sinking object. Herein, the heat sinking object may include an imaging device, for example, an X-ray imaging device. However, the exemplary embodiments are not limited thereto, for example, the heat sinking object may further include a drive means to rotate the imaging device in the heat sinking space 300, and the like. Air introduced via the air introducing portion 100 can flow into the heat sinking space 300, and exchanges heat with the heat sinking object. Then, the air which has exchanged heat with the heat sinking object can flow into the capture portion 500 and is captured by the capture portion 500.

The capture portion 500 can be in communication with the heat sinking space 300 and the air discharge portion 700. The capture portion 500 can capture air which flows from the heat sinking space 300 to the capture portion 500, and can cause the captured air to flow into the air discharge portion. That is, the capture portion 500 can allow air to flow in a first direction from the heat sinking space 300 to the air discharge portion 700 and can prevent the air from flowing in a second direction from the air discharge portion 700 to the heat sinking space 300 and opposite to the first direction.

To this end, the capture portion 500 can include a plurality of capture guide members 510.

The capture portion 500 may be disposed adjacent to the heat sinking space 300, for example, the capture portion 500 is disposed on a periphery of the heat sinking space 300. The plurality of capture guide members 510 in the capture portion 500 can surround the heat sinking space 300. As such, when the heat sinking object rotates in the heat sinking space 300, air in the heat sinking space 300 can flow from the heat sinking space 300 to the capture portion 500 disposed on the periphery of the heat sinking space 300 due to a centrifugal force, and thus, is guided by the capture guide members 510 to flow into the air discharge portion 700 in a single direction (i.e., a first direction).

Figure 7:
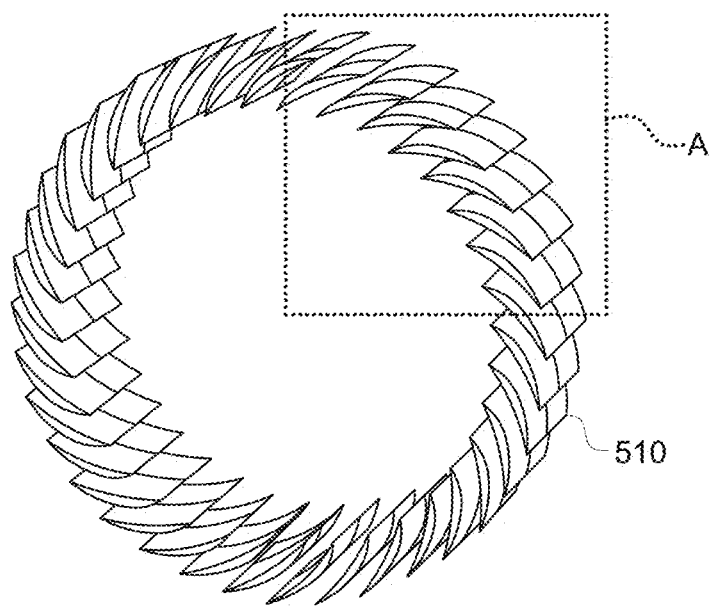
FIG. 7 is a perspective view illustrating capture guide members of a heat sinking system according to an exemplary embodiment.
Figure 8:
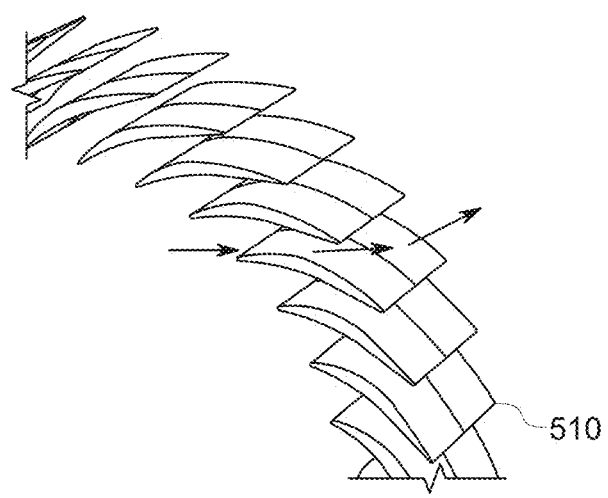
FIG. 8 is an enlarged view illustrating part A in FIG. 7.

Next, capture guide members are described in detail with reference to FIGS. 7 and 8. FIG. 7 is a perspective view illustrating the capture guide members of a heat sinking system according to an exemplary embodiment. FIG. 8 is an enlarged view illustrating part A in FIG. 7. As shown in FIG. 7, the plurality of capture guide members 510 may have a leaf-like shape, so that a LAVAL pipe allowing air to flow in a single direction (i.e., a first direction) can be formed between two adjacent capture guide members 510. As such, air can flow from the capture portion 500 to the air discharge portion 700 as shown in the arrows of FIG. 8.

In an exemplary embodiment, in order to enable air in an air introducing portion 100 to flow into heat sinking space 300 instead of flowing into a capture portion 500 disposed on a periphery of and in communication with the heat sinking space 300, a heat sinking system can include a first blocking member 200.

Figure 9:
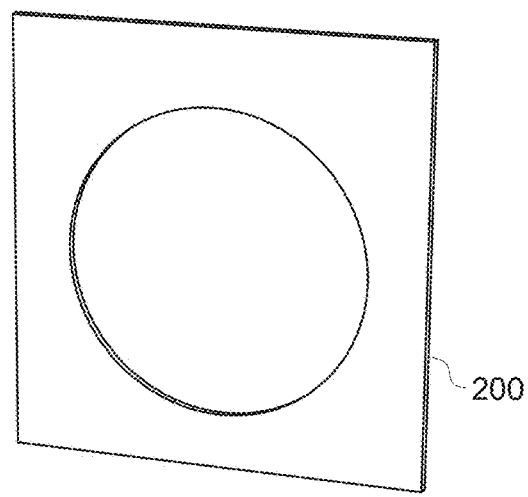
FIG. 9 is a perspective view illustrating a first blocking member of a heat sinking system according to an exemplary embodiment.
Figure 10:
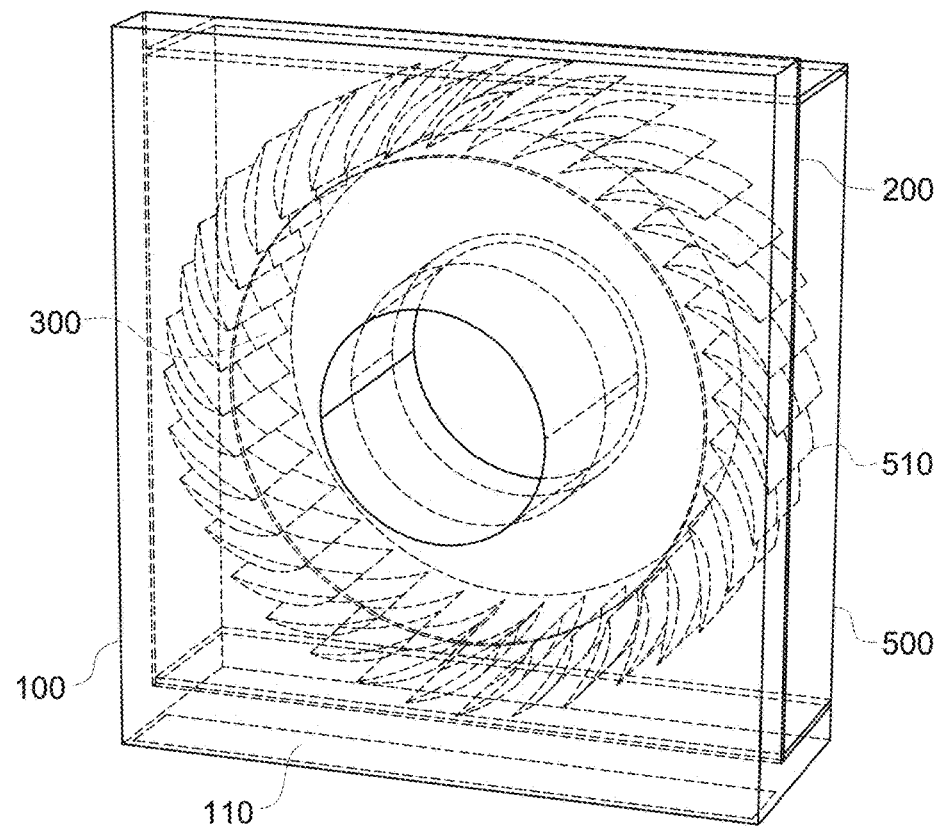
FIG. 10 is a perspective view illustrating a state in which an air introducing portion, a capture portion and a first blocking member of a heat sinking system according to an exemplary embodiment are assembled together.

FIG. 9 is a perspective view illustrating a first blocking member of a heat sinking system according to an exemplary embodiment. FIG. 10 is a perspective view illustrating a state in which an air introducing portion, heat sinking space, a capture portion and a first blocking member according to an exemplary embodiment are assembled together. As shown in FIGS. 9 and 10, a first blocking member 200 may be provided between an air introducing portion 100, and heat sinking space 300 and a capture portion 500, so as to allow air to flow into the heat sinking space 300 and prevent the air from flowing into the capture portion 500. In addition, capture guide members 510 in the capture portion 500 can be secured to the first blocking member 200.

An air discharge portion 700 may be in communication with the capture portion 500, thereby discharging air which flows in out of the capture portion 500 to external. For example, the air discharge portion 700 may include an air outlet 710 disposed at the top of the heat sinking system. However, the exemplary embodiments are not limited thereto, for example, the air outlet 710 may be provided at different positions as needed, and a plurality of air outlets 710 may be provided.

Figure 11:
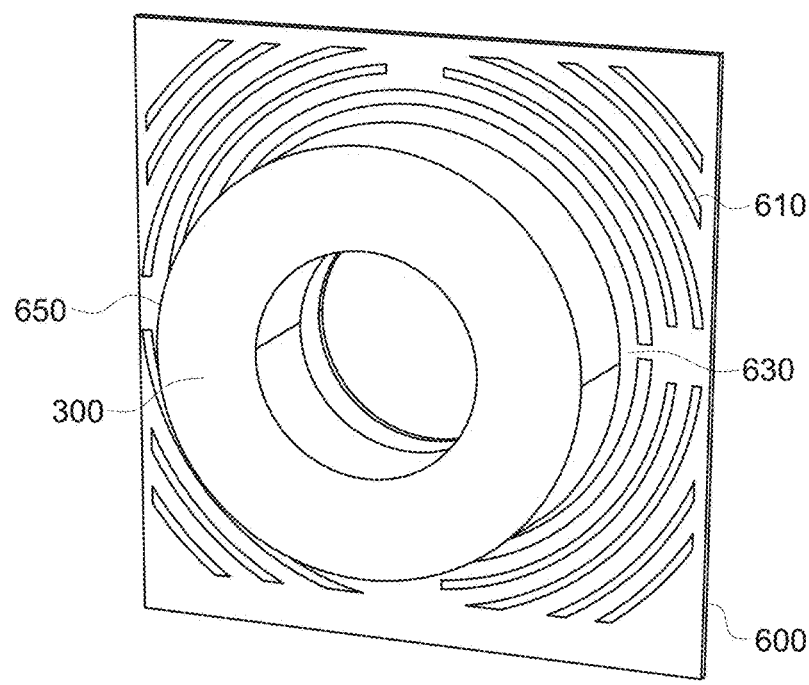
FIG. 11 is a perspective view illustrating a second blocking member of a heat sinking system according to an exemplary embodiment.
Figure 12:
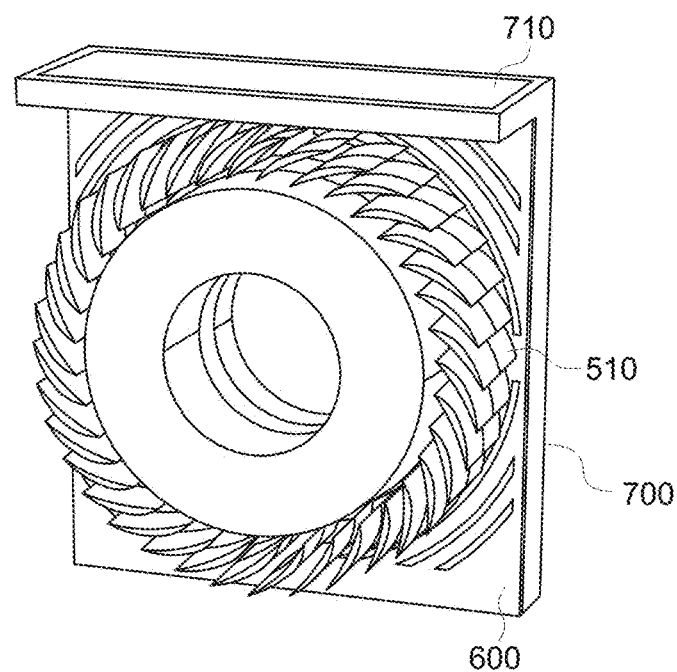
FIG. 12 is a perspective view illustrating a state in which capture guide members, a second blocking member and an air discharge portion of a heat sinking system according to an exemplary embodiment are assembled together.

In an exemplary embodiment, a heat sinking system may further comprise a second blocking member 600. FIG. 11 is a perspective view illustrating a second blocking member of a heat sinking system according to an exemplary embodiment. FIG. 12 is a perspective view illustrating a state in which capture guide members, a second blocking member and an air discharge portion of a heat sinking system according to an exemplary embodiment are assembled together. As shown in FIGS. 11 and 12, the second blocking member 600 may be disposed between an air discharge portion 700, and heat sinking space 300 and a capture portion 500. The second blocking member 600 may comprise an opening area 610 corresponding to the capture portion 500, and a blocking area 630 corresponding to the heat sinking space 300. Further, the second blocking member 600 may further include a support 650 disposed in the blocking area 630 and configured to support a heat sinking object in the heat sinking space 300. Herein, the opening area 610 may include a plurality of openings with patterns as shown in FIG. 11. However, the exemplary embodiments are not limited thereto, and the patterns of the plurality of openings can be designed to have various shapes, for example, strip shape, as needed.

Figure 13:
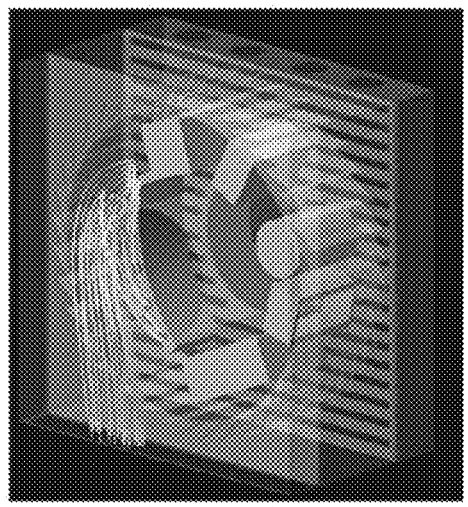
FIG. 13 is a diagram illustrating simulation results of air flow of a heat sinking system according to an exemplary embodiment and air flow of an existing heat sinking system.
Figure 13:
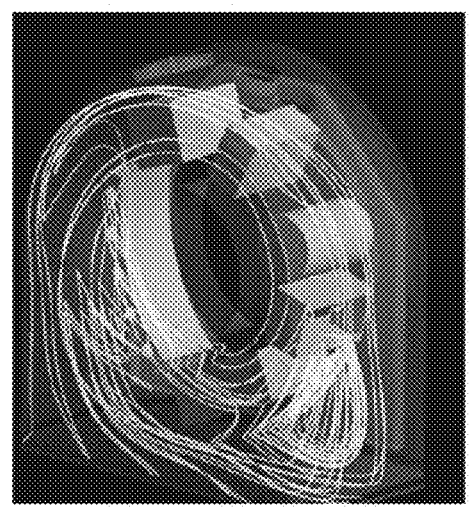

FIG. 13 is a diagram illustrating simulation results of air flow of a heat sinking system according to an exemplary embodiment and air flow of an existing heat sinking system. As shown in (a) of FIG. 13, in the heat sinking system according to the exemplary embodiment, air enters heat sinking space from an air inlet via an air introducing portion, and exchanges heat with a heat sinking object in the heat sinking space, before flowing into a capture portion and being captured by the capture portion, thereby flowing into an air discharge portion in a single direction and ultimately being discharged to external. In other words, air backflow is allowed not to occur in the heat sinking system according to the exemplary embodiment. However, as shown in (b) of FIG. 13, in the existing heat sinking system, air backflow occurs. For example, a part of the air after exchanging heat with the heat sinking object flows back to an air inlet. As can also be seen from a comparison of two simulation results, a path of air flow in the heat sinking system according to the exemplary embodiment can be shorter than that in the existing heat sinking system. Thus, as compared with the existing heat sinking system, the heat sinking system according to the exemplary embodiment can have greater heat sinking efficiency.

Figure 14:
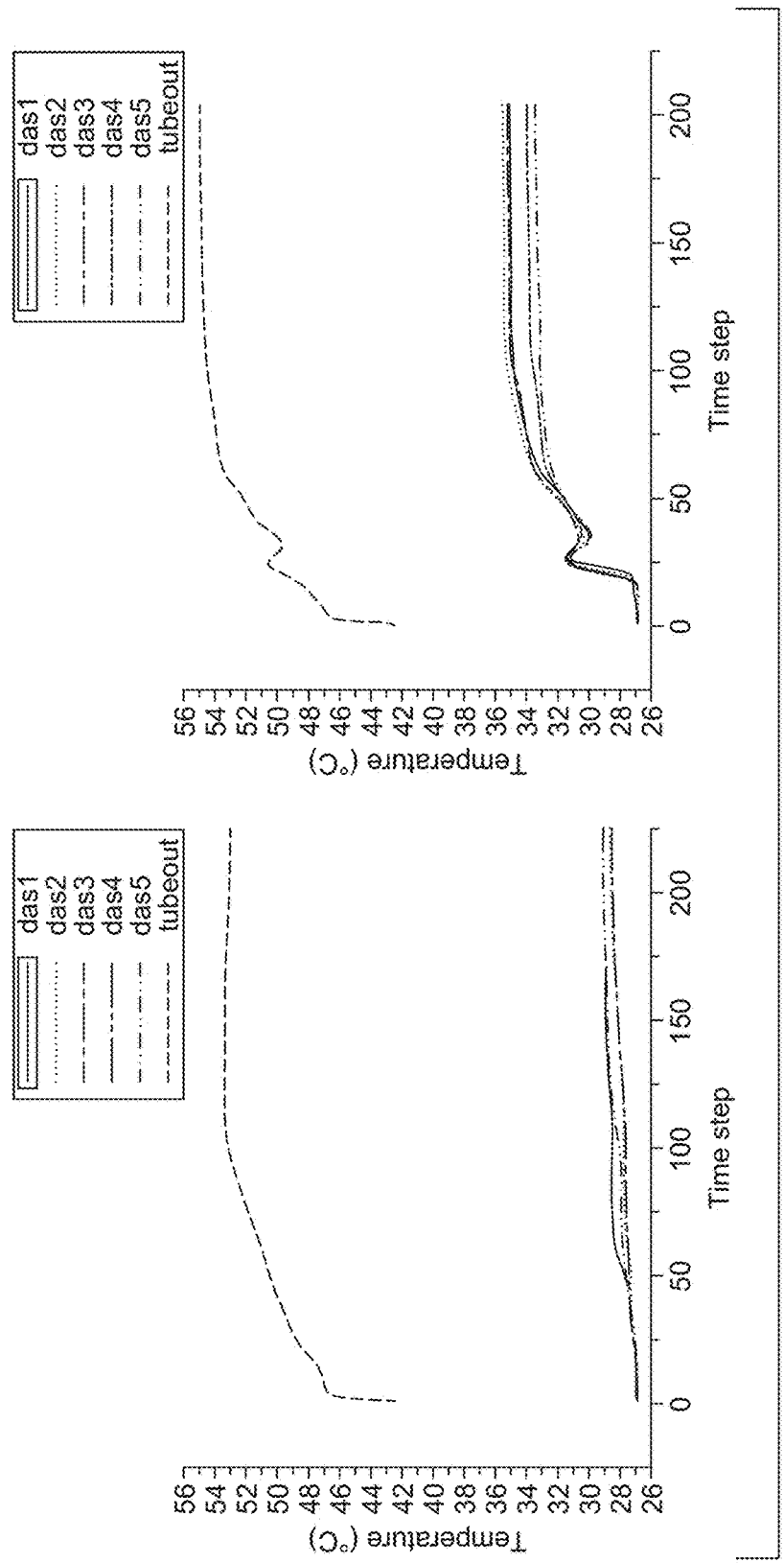
FIG. 14 is a curved diagram illustrating variation of temperature along with time for a heat sinking system according to an exemplary embodiment and variation of temperature along with time for an existing heat sinking system.

FIG. 14 is a curved diagram illustrating variation of temperature along with time for a heat sinking system according to an exemplary embodiment and variation of temperature along with time for an existing heat sinking system, in which the various curves respectively represent variation of temperature along with time as measured at monitoring points das1, das2, das3, das4, das5 and tubeout of the heat sinking system according to the exemplary embodiment and variation of temperature along with time as measured at monitoring points das1, das2, das3, das4, das5 and tubeout of the existing heat sinking system. In FIG. 14, the abscissa represents time step, i.e., represents a small time unit (zero dimension) of a simulation operation. By comparison between FIG. 14($a$) illustrating a curved view of the variation of temperature along with time for the heat sinking system according to the exemplary embodiment and FIG. 14($b$) illustrating a curved view of the variation of temperature along with time according to the existing heat sinking system, it can be seen that, under the same operating conditions, temperature of the heat sinking system according to the exemplary embodiment can be about 5° C. lower than that according to the existing heat sinking system.

Figure 15:
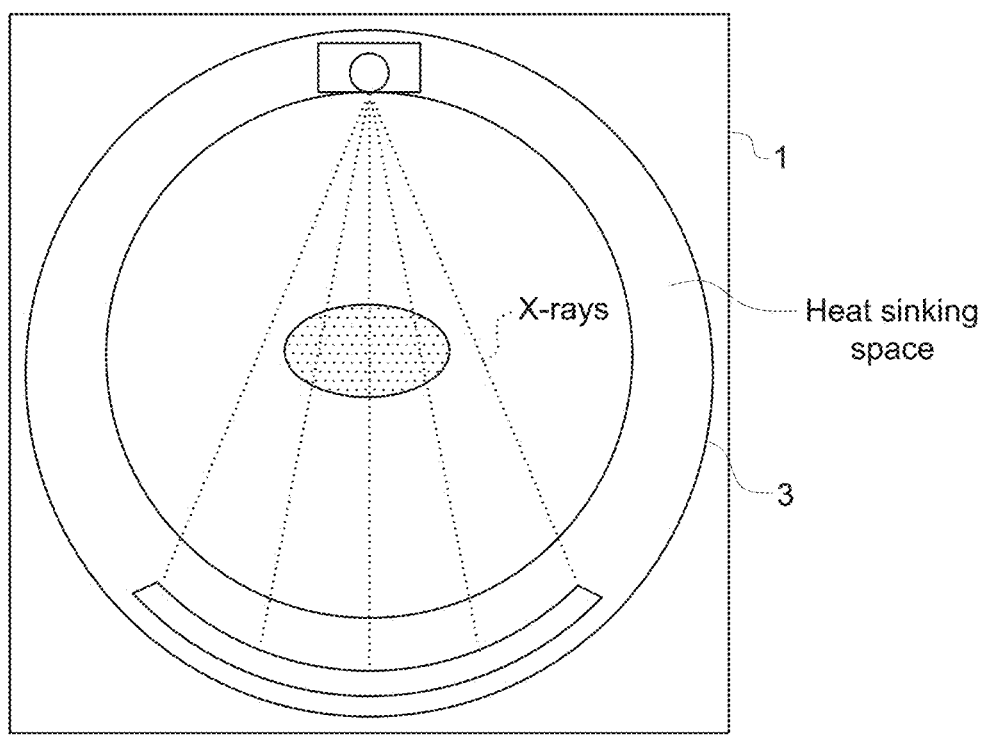
FIG. 15 is a schematic view illustrating an imaging apparatus according to an exemplary embodiment.

FIG. 15 is a schematic view illustrating an imaging apparatus according to an exemplary embodiment. As shown in FIG. 15, the imaging apparatus may include a gantry 1, and an imaging device 3 disposed and accommodated in the gantry 1. The gantry 1 may include a heat sinking system as described with reference to the above exemplary embodiments. In this case, the imaging device 3 may be provided and accommodated in heat sinking space of the heat sinking system as a heat sinking object, to exchange heat with air which flows in out of an air introducing portion.

Additionally, the imaging device can further include a driver (not shown) which drives the imaging device 3 to rotate the imaging device 3 in the heat sinking space. As such, the imaging device 3 can scan an aim object to acquire an image of the aim object, while being in rotation.

According to an exemplary embodiment, an imaging apparatus can be a CT apparatus. In the exemplary embodiment, an imaging device 3 can include an X-ray generator to generate X-rays and emit the generated X-rays to an aim object, and an X-ray detector to receive X-rays passing through the aim object and convert the received X-rays into electrical signals. In addition, although not shown, the imaging apparatus may further comprise a processor for receiving the electrical signals generated by the X-ray generator and processing the received electrical signals to generate an image, a display for displaying the generated image, and the like.

According to an exemplary embodiment, since air backflow is allowed not to occur in a heat sinking system and/or a path of air flow is relatively short, it is possible to perform more efficient heat sinking on such elements as an imaging device of an imaging apparatus, disposed in heat sinking space of the heat sinking system. In addition, the imaging apparatus and its heat sinking system according to the exemplary embodiment have simple structure while conforming to the principles of aerodynamics and heat transfer, so as to facilitate upgrading and reforming based on the existing imaging device, thereby making it possible to save costs.

Some exemplary embodiments have been described above. However, it should be understood that, various modifications may be made. For example, if techniques as described are implemented in different orders and/or if components in a system, framework, device, or circuit as described are combined in different manners and/or are replaced or supplemented by other components or other equivalents, appropriate results can be realized. Correspondingly, other embodiments also fall within the protection scope of the claims.

What is claimed is:

1. A heat sinking system comprising:
   an air introducing portion, a capture portion and an air discharge portion, wherein,
   the air introducing portion is configured to introduce air from external, and to be in communication with heat sinking space, so that the introduced air flows into the heat sinking space and exchanges heat with a heat sinking object which is accommodated in the heat sinking space;
   the capture portion is configured to be in communication with the heat sinking space and the air discharge portion, and to capture air which flows from the heat sinking space to the capture portion and enable the captured air to flow into the air discharge portion;
   the air discharge portion is configured to discharge the air which flows in out of the capture portion to the external; and
   a first blocking member disposed between the air introducing portion, and the heat sinking space and the capture portion and configured to block the air introduced from the air introducing portion from flowing into the capture portion.

2. The heat sinking system according to claim 1, wherein the air introducing portion includes an air inlet disposed at the bottom of the heat sinking system.

3. The heat sinking system according to claim 1, wherein the capture portion comprises a plurality of capture guide members, the plurality of capture guide members being configured to allow air in the capture portion to flow in a first direction from the heat sinking space to the air discharge portion and to prevent the air in the capture portion from flowing in a second direction from the air discharge portion to the heat sinking space and opposite to the first direction.

4. The heat sinking system according to claim 3, wherein said plurality of capture guide members is configured to have a leaf-like shape, so that a LAVAL pipe allowing air to flow in the first direction is formed between two adjacent capture guide members.

5. The heat sinking system according to claim 4, wherein said plurality of capture guide members is disposed around the heat sinking space.

6. The heat sinking system according to claim 1, wherein the heat sinking system further comprises:
   a second blocking member disposed between the air discharge portion, and the heat sinking space and the capture portion and configured to block air in the heat sinking space from flowing into the air discharge portion.

7. The heat sinking system according to claim 6, wherein the second blocking member comprises an opening area corresponding to the capture portion, a blocking area corresponding to the heat sinking space, and a support which is disposed within the blocking area and configured to support the heat sinking object in the heat sinking space.

8. The heat sinking system according to claim 7, wherein the air discharge portion comprises an air outlet disposed at the top of the heat sinking system.

9. The heat sinking system according to claim 1, the heat sinking system further comprising at least one of a first fan and a second fan, wherein the first fan is disposed at the air introducing portion for blowing air from the external to the air introducing portion, and the second fan is disposed at the air discharge portion for blowing air in the air discharge portion to the external.

10. An imaging apparatus, comprising:
    a gantry configured to include the heat sinking system according to claim 1; and
    an imaging device disposed and accommodated in heat sinking space of the heat sinking system as a heat sinking object, to exchange heat with air which flows in out of the air introducing portion.

11. The imaging apparatus according to claim 10, wherein the imaging device is configured to scan an aim object to acquire an image of the aim object, while being in rotation.

12. The imaging apparatus according to claim 11, wherein the imaging device comprises:
    an X-ray generator configured to generate X-rays and emit the generated X-rays to the aim object; and
    an X-ray detector configured to receive X-rays passing through the aim object and convert the received X-rays into electrical signals.

* * * * *